(12) United States Patent
Lakhan et al.

(10) Patent No.: US 9,593,930 B2
(45) Date of Patent: Mar. 14, 2017

(54) APPARATUS AND METHOD FOR MEASURING DEPOSITS INSIDE A TUBE

(76) Inventors: Richard Lakhan, Pembroke (CA);
 Brian Lepine, Petawawa (CA); Joseph Renaud, Chalk River (CA); Laurie Davey, Chalk River (CA)

( * ) Notice: Subject to any disclaimer, the term of this patent is extended or adjusted under 35 U.S.C. 154(b) by 1277 days.

(21) Appl. No.: 13/380,233

(22) PCT Filed: Jun. 25, 2010

(86) PCT No.: PCT/CA2010/000942
§ 371 (c)(1),
(2), (4) Date: Jul. 31, 2012

(87) PCT Pub. No.: WO2010/148487
PCT Pub. Date: Dec. 29, 2010

(65) Prior Publication Data
US 2013/0009634 A1  Jan. 10, 2013

(51) Int. Cl.
*G01N 27/72* (2006.01)
*G01R 33/12* (2006.01)
(Continued)

(52) U.S. Cl.
CPC ............. *G01B 7/06* (2013.01); *B24B 49/105* (2013.01); *F22B 37/10* (2013.01); *G01N 27/902* (2013.01);
(Continued)

(58) Field of Classification Search
CPC ...... G01N 27/82; G01N 27/72; G01N 27/902; G01N 27/9046; G01N 27/90; G01R 33/12; G01B 7/00
USPC ....... 324/242, 238, 220, 221, 239, 243, 262, 324/241, 219, 229, 207, 208, 37, 40
See application file for complete search history.

(56) References Cited

U.S. PATENT DOCUMENTS

| | | | |
|---|---|---|---|
| 4,292,588 A * | 9/1981 | Smith | G01B 7/10 324/221 |
| 4,942,545 A * | 7/1990 | Sapia | G01N 27/9086 324/202 |

(Continued)

FOREIGN PATENT DOCUMENTS

| | | |
|---|---|---|
| CA | 1202368 | 3/1986 |
| GB | 1355607 | 6/1974 |

(Continued)

OTHER PUBLICATIONS

Romanian Office Action dated Jul. 29, 2015 issued in Romanian Patent Application No. a201101445, and an English translation thereof.

(Continued)

*Primary Examiner* — Patrick Assouad
*Assistant Examiner* — Taqi Nasir
(74) *Attorney, Agent, or Firm* — Norton Rose Fulbright Canada LLP (57) ABSTRACT

The present invention provides a probe apparatus and an associated method for measuring a magnetite deposit thickness, which apparatus and method is independent of the porosity and magnetic permeability of the magnetite deposit. The probe apparatus of this invention is an axial scanning and inside surface-following probe that can accurately and reliably measure the inside diameter of a tube. The probe apparatus of the present invention optionally comprises two modules: the first module is the surface-following module and the second module is a conventional eddy current probe.

14 Claims, 11 Drawing Sheets

(51) Int. Cl.

| | | |
|---|---|---|
| G01B 7/06 | (2006.01) | |
| B24B 49/10 | (2006.01) | |
| F22B 37/10 | (2006.01) | |
| G01N 27/90 | (2006.01) | |
| G21C 17/017 | (2006.01) | |
| G21D 1/00 | (2006.01) | |
| F28F 19/00 | (2006.01) | |
| F28G 15/00 | (2006.01) | |

(52) U.S. Cl.
CPC .......... *G21C 17/017* (2013.01); *G21D 1/006* (2013.01); *F28F 19/00* (2013.01); *F28G 15/00* (2013.01); *Y02E 30/40* (2013.01)

(56) References Cited

U.S. PATENT DOCUMENTS 5,247,251 A    9/1993  Yost et al.

2004/0257072 A1 * 12/2004 Samson ............... G01N 27/902
                                                        324/242
2009/0123778 A1 *  5/2009 Russell ............. B23K 20/1235
                                                        428/661

FOREIGN PATENT DOCUMENTS

GB          2204699         11/1988
HR    WO 2006087592 A1 *  8/2006  .............. F16L 55/28

OTHER PUBLICATIONS

Chinese Patent Office, First Office Action dated Jan. 6, 2014, issued in Chinese Patent Application No. 201080036557.0, and an English translation thereof.
International Search Report dated dated Sep. 17, 2010 from PCT/CA2010/000942.
Written Opinion of the International Searching Authority dated Sep. 17, 2010 from PCT/CA2010/000942.

* cited by examiner

| Examination Technique Specification Sheet (ETSS) Estimation of ID Magnetite Thickness with the ADAM Probe |||||||||
|---|---|---|---|---|---|---|---|---|
| Document: | | | | | Revision 0 | | Page: 1 of 11 ||
| Site: Bruce Nuclear Generating Station (BNGS) |||||||||
| Examination Scope |||||||||
| This technique is applicable for estimating ID thickness in 12.9 mm diameter Inconel 600 SG tubing with the ADAM probe. |||||||||
| Instrument |||| Tubing |||||
| Manufacturer/Model: Zetec MIZ-80 iD |||| Material Type: Inconel 600 |||||
| Data Recording Equipment |||| OD/Wall (in): 0.51" OD x 0.044 Wall  (mm): 12.9 mm OD x 1.1 mm |||||
| Unix compatible hard drive with at least 30Gbyte space |||| Calibration Standards |||||
| ^ |||| Type:  Calibration Tube (Supplied) Minimum requirements are: 1. Six various diameter reductions. |||||
| Software |||| Additional Calibration Tubes: Standard Bobbin ASME calibration tube. |||||
| Manufacturer: Zetec |||| ^ |||||
| Version/Revision: Eddynet Suite 3.1.6 |||| ^ |||||
| | | | | Analog Signal Path |||||
| Examination Procedure |||| Probe Extension Manuf.: N/A |||||
| Number/Revision: N/A |||| Extension Type & Length: N/A |||||
| Scan Parameters |||||||||
| Digitization Rate, Samples per Inch(min) || SPI | Axial Direction | N/A | Circ. Direction || N/A ||
| Recording Speed || Sample Rate | RPM Set | RPM Min || RPM Max. |||
| 18 IPS (Nominal) || 1000 SPS | N/A | N/A || N/A |||
| 18 IPS (Maximum) || 1000 SPS | N/A | N/A || N/A |||
| Probe |||||||||
| Description (Model/Probe Diameter/Number of Coils) |||| Manufacturer/Part Number ||| Length ||
| ADAM / .390"-.430" / 4 |||| AECL / F01-380-001 ||| 15.24 m (50') ||
| Data Acquisition |||||||||
| Calibration Channels |||||||||
| Channel Name | Frequency (kHz) | Coil | Gain (dB) | Probe | DRV Volts | Set Phase On | Set Phase To | Deflect |
| 1 | 480 | 1 | 38 | DIFF | 12.0 | ID groove | Horizontal | Right |
| 2 | 480 | 5 | 28 | ABSL | 12.0 | ID groove | Horizontal | Left |
| 3 | 240 | 1 | 38 | DIFF | 12.0 | ID groove | Horizontal | Right |
| 4 | 240 | 5 | 28 | ABSL | 12.0 | ID groove | Horizontal | Left |
| 5 | 120 | 1 | 38 | DIFF | 12.0 | ID groove | Horizontal | Right |
| 6 | 120 | 5 | 28 | ABSL | 12.0 | ID groove | Horizontal | Left |
| 7 | 30 | 1 | 38 | DIFF | 12.0 | ID groove | Horizontal | Right |
| 8 | 30 | 5 | 28 | ABSL | 12.0 | ID groove | Horizontal | Left |
| 9 | 480 | 2 | 38 | ADAM | 10.0 | Dent | Vertical | N/A |
| 10 | 240 | 2 | 38 | ADAM | 10.0 | Dent | Vertical | N/A |
| 11 | 120 | 2 | 38 | ADAM | 10.0 | Dent | Vertical | N/A |
| 12 | 30 | 2 | 38 | ADAM | 10.0 | Dent | Vertical | N/A |
| Data acquisition Setup is shown on following configuration tables. |||||||||

APPARATUS AND METHOD FOR MEASURING DEPOSITS INSIDE A TUBE

FIELD OF THE INVENTION

The present invention generally relates to an apparatus and method for inspecting the inner wall of a conduit, and more particularly relates to an apparatus and method for detecting and measuring deposits on the inner wall of a conduit, such as steam generator or heat exchanger tubing.

BACKGROUND

A characteristic of CANDU® steam generator tubes is that they have protective deposits of magnetite on the internal diameter (ID) surfaces. There is currently no method that accurately and reliably measures the thickness of magnetite deposited on the ID of steam generator tubing.

Probes for inspecting the inner walls of metallic conduits are known in the prior art. Such probes are particularly useful in inspecting the internal walls of heat exchangers in nuclear steam generators for flaws or deformation caused by corrosion, fretting, or the accumulation of sludge products in the crevice regions of the generator. Generally, these probes operate by means of either strain gauges, or eddy current probes.

Strain gauge-type probes are generally formed from a cylindrical mandrel that is circumscribed by a plurality of the spring-loaded fingers. Strain gauges are placed onto each of the spring-loaded fingers. When the probe body is inserted into the interior of a tube and translated along its longitudinal axis, differences in the radius of the internal tube walls cause one or more of the spring fingers to flex in a radial direction. The extent to which these fingers flex is picked up by the strain gauges attached to the fingers.

Eddy current probes are generally formed by an eddy current coil resiliently mounted in a probe head so as to wipingly engage the interior of the tube being inspected when the probe is rotated. The coil is electrically connected to a current generator which conducts an alternating current to the coil as it is moved. An impedance detecting circuit is also connected across the leads of the coil. In operation, the alternating current conducted through the coil excites it into generating a pulsating magnetic field whose magnitude and polarity changes in accordance with the frequency of the current. When the coil of the probe is positioned in the vicinity of an electrically conductive wall, the changing magnetic flux emanating from the coil induces eddy currents in a portion of the wall. The particular amperage, voltage and direction of the eddy currents produced are dependent in part upon the specific impedance of the portion of the wall that conducts the eddy current. Because the direction of flow of the eddy currents generated by the coil is opposite to the current flowing through the probe sensing coil, the magnetic field created by the eddy currents creates an impedance in the sensing coil. The strength of these eddy currents is in turn dependent upon the resistance that these currents encounter as they circulate through the wall. Since flaws in the metal wall (such as cracks, pits or regions of local thinning) create regions of higher resistances at flaw locations, eddy current probes can be used to locate flaws by constantly monitoring the impedances of the sensing coils as the probe body is moved along the internal walls of the tube.

While some prior art probes are capable of performing satisfactory inspections of heat exchanger tubes, they each suffer from drawbacks that have limited their usefulness. In addition, these probes do not permit measurement of a deposit on the ID surfaces.

Strain gauge-type probes tend to be delicate since they require the mounting of very small strain gauges onto the resilient metal fingers that circumscribe the probe body. Both the strain gauges themselves and their lead wires are prone to breakage if the probe is subjected to inadvertent mechanical shock, or is even rapidly drawn through an unusually rough portion of tube. While strain gauge-type probes are capable of detecting the presence of ovality in such tubes (which in turn indicates if the tube has been stressed as a result of intense, localized pressure), the flaw resolution of many of these types of profilometers is relatively coarse. If the flaw resolution is increased by the addition of more spring fingers and strain gauges around the circumference of the probe, the gauges must be made even smaller, which increases the fragility of the device further.

Eddy current type probes can also suffer from excessive fragility in designs where a tiny coil resiliently engages the interior of a wall in wiping contact. While some of the better probe designs overcome this defect by either putting the eddy current probe in a self-lubricating plastic (which is subject to wear), or by attaching the coil to the back of a stylus which resiliently engages the inner tube wall as the probe is translated therein, none of these designs, is capable of accurately resolving tube ovality, or measuring deposits on the ID.

Furthermore, measurement of a magnetite deposit layer is made more difficult because the magnetite layer has variable physical properties that affect current methods, such as conventional eddy current. The magnetic permeability and porosity of magnetite are the primary sources of these problems.

An eddy current method of measuring the magnetite layer has been developed in the past by the present Applicant. The method comprises use of an eddy current bobbin probe, excited by conventional means with a single high frequency, that records the change in the signal referenced from a portion of the tube lacking magnetite deposits. This method was developed using tube samples pulled from the field to establish a relationship between thickness and voltage. The measurements are then based on an assumed value for permeability, obtained from these pulled tubes. Thus, if the magnetic or physical properties of the layer change from tube to tube, then the eddy current response will differ, resulting in less accurate thickness estimates. Any variations in permeability of the magnetite found in the tubes evaluated in the field would cause significant errors in the estimations of thickness. With the eddy current bobbin probe technique it is not possible to separate thickness and permeability effects.

Another measurement method, the Oxiprobe™, uses the mass of the loading and the area cleaned to derive a value for the thickness [Gonzalez, F., Brennenstuhi, A. M., Palumbo, G. and Dyck, R. W., "Steam Generator Primary Side Fouling Determination Using the Oxiprobe Inspection Technique", Fourth International Conference On CANDU Maintenance, Toronto, 1997 Nov. 16-18]. With this method, the magnetite was also assumed to have a certain, consistent, density.

U.S. Pat. No. 4,876,506, describes an apparatus and method for inspecting the profile of the inner wall of a tube employing a wall follower and an eddy current probe. The disclosed apparatus includes (i) a cylindrical probe body that is insertable within the tube, (ii) a probe assembly disposed within the probe body that includes an eddy current sensing coil and a copper plate which are movable with respect to one another, and (iii) a wall follower assembly including a stylus on one end and which is linked to the probe assembly on its other end for converting changes in the radius of the tube wall into changes in the distance between the eddy current sensing coil and the copper plate.

The probe of U.S. Pat. No. 4,876,506 is not an axial-scanning probe. Further, the probe cannot be extended for use for anything other than the inside diameter of the tube and, thus, cannot measure the thickness of any inside deposits on the tube wall. Third, the eddy currents from this module are coupled with the actual tube itself.

There remains a need for an apparatus and method that accurately and reliably measures deposits, such as magnetite, on the ID of steam generator tubing.

This background information is provided for the purpose of making known information believed by the applicant to be of possible relevance to the present invention. No admission is necessarily intended, nor should be construed, that any of the preceding information constitutes prior art against the present invention.

SUMMARY

The present application relates to an apparatus and method for measuring deposits inside a tube.

In accordance with one aspect, there is provided a probe apparatus comprising a surface-following probe, said surface-following probe comprising: a probe body; one or more shoe pairs, wherein each shoe pair consists of a biased shoe attached to said probe body and a fixed shoe attached to said probe body; a target mounted on the biased shoe of each of said one or more shoe pairs, wherein said target consists of a material that is conductive and ferromagnetic, conductive and non-ferromagnetic, or non-conductive and ferromagnetic; and a conductor coil electromagnetically coupled with each target.

In accordance with another aspect, there is provided a method of determining the thickness of an inside diameter, conductive deposit within a tube, said method comprising the steps of (i) determining the internal diameter of the tube at a location within the tube; (ii) performing eddy current testing at the location; and (iii) correlating the internal diameter determined in step (i) with the output from step (ii) to calculate the thickness of the inside diameter, conductive deposit within the tube.

In accordance with another aspect, there is provided a kit for use in determining the thickness of an inside diameter, conductive deposit within a tube, said kit comprising (i) a probe apparatus comprising a surface-following probe coupled to an eddy-current probe; and (ii) one or more calibration tubes.

BRIEF DESCRIPTION OF THE FIGURES

FIG. 4 depicts an example of an examination technique specification sheet (ETSS) that describes the data acquisition process for a probe apparatus according to one embodiment of the present invention.

DETAILED DESCRIPTION OF THE INVENTION

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

Described herein is a probe apparatus and an associated method for measuring the thickness of an internal deposit within a tube, which apparatus and method functions independent of the porosity and permeability of the deposit. In a specific, exemplary embodiment, the internal deposit is a magnetite deposit and the apparatus and method functions independent of the porosity and magnetic permeability of the magnetite. The probe apparatus is an axial scanning and inside surface-following probe that can accurately and reliably measure the inside diameter of a tube.

In the remainder of the description, consideration will be given to a non-limitative embodiment of an application of the process of the invention to the inspection of steam generator tubes and measurement of the thickness of inside diameter magnetite within the tubes. However, obviously other applications are possible within the scope of the inspection of internal diameter conductive material in generally cylindrical equipment.

Figure 1:
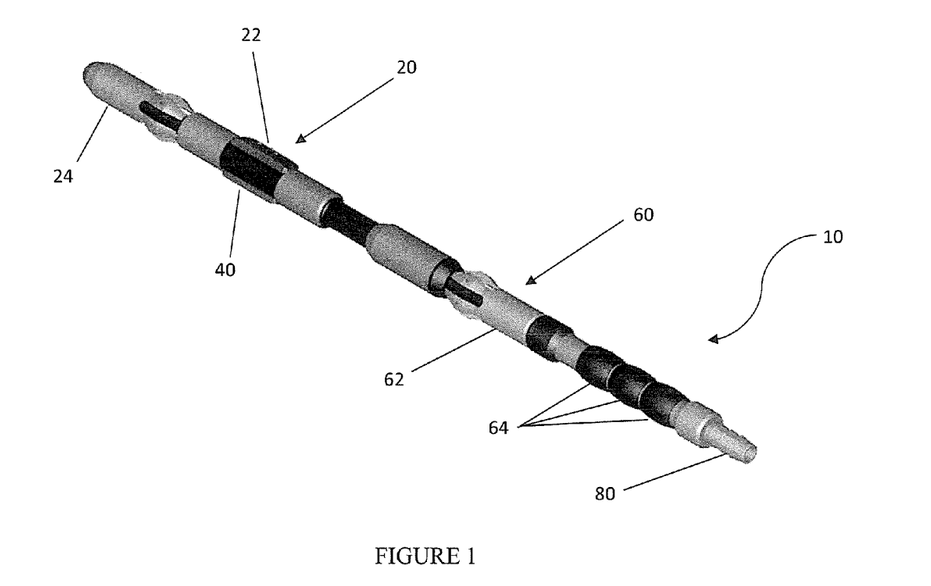
FIG. 1 depicts the layout of a probe apparatus according to one embodiment of the present invention.

Referring to FIG. 1, the probe apparatus 10 of the present invention comprises of two modules and a push-tube (not shown). The first module is the surface-following module 20. In accordance with one embodiment of the present invention, the first module acts as a stand alone probe. In accordance with an alternative embodiment of the invention, the first module 20 is used in combination with the second module 60 in the same probe head whereby the first module output is used to calibrate the output of the second module.

Surface-Following Module

Figure 2A:
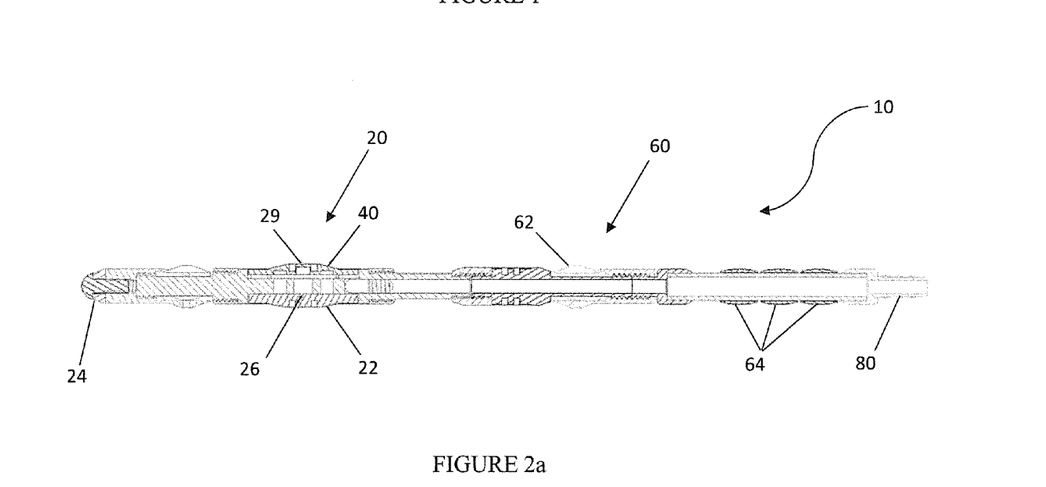
FIG. 2a is a cross-sectional schematic of the probe apparatus depicted in FIG. 1
Figure 2B:
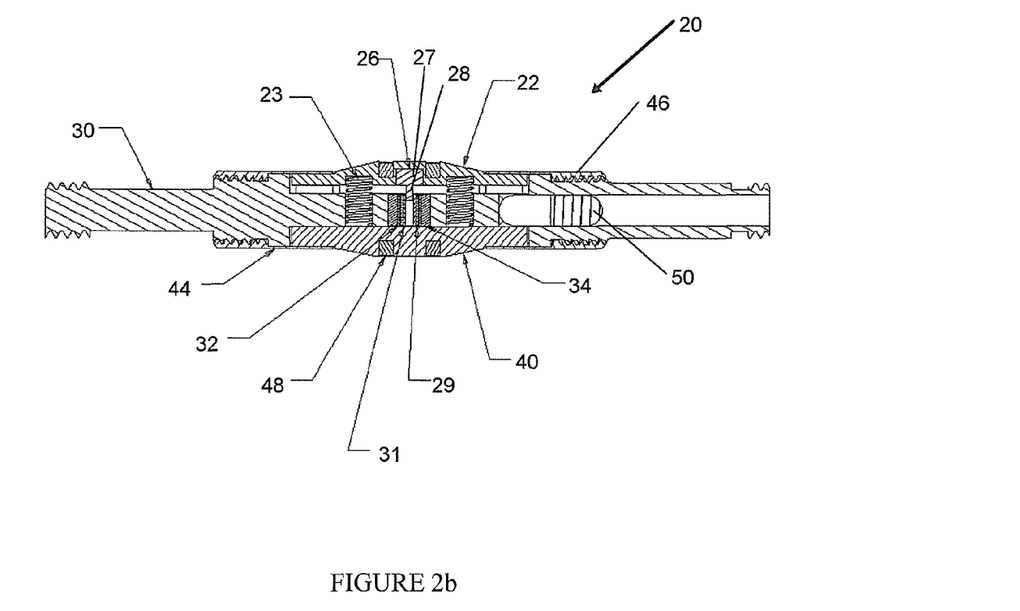
FIG. 2b is a detailed schematic of the surface-following module of the probe apparatus depicted in FIG. 2b.

As depicted in FIGS. 1 and 2, the first, surface-following, module 20 consists of a biased shoe 22 that is positioned behind front guide 24 at the leading end of probe apparatus 10. Biased shoe 22 rides along the tube wall as the probe is pushed or pulled through the tube. In accordance with one embodiment of the present invention, biased shoe 22 is spring mounted. For example, as shown in FIG. 2b, two springs 23 are mounted in body 30 and bias shoe 22 outward, to facilitate contact of shoe 22 with internal surface of the tube during testing.

Although first module 20 is characterized above as including a spring-mounted shoe 22, alternative means of biasing the surface-following shoe can be incorporated into first module 20 in place of a spring. Such biasing means are selected based on their ability to permit the surface of the shoe to remain in contact with the internal surface of the tube.

A puck-shaped or cylindrical, or a combination thereof, material is mounted into the shoe, and acts as a target 26 for a conductor coil 29, which is itself rigidly affixed to body 30 of the probe.

As shown in FIG. 2(b), the combination form of the target can be shaped as a puck 27 with a protruding smaller cylinder 28. In this configuration cylinder 28, (optionally referred to as the plunger), has a diameter smaller than the inner diameter of the sleeved conductor coil 29 to allow cylinder 28 to plunge into the top of conductor coil 29 to maximize the electromagnetic coupling between target 26 and the coil 29.

Target 26 can be manufactured from ferrite, steel, or any other material that is either conductive and ferromagnetic, or conductive and non-ferromagnetic, or non-conductive and ferromagnetic. The material from which target 26 is manufactured is selected to have a high relative magnetic permeability.

Conductor coil 29 is protected from any potential abrasions from plunger 28 with the inclusion of a thin inner sleeve 31 within coil 29. Coil 29 is wound onto inner sleeve 31. Optionally, coil 29 is put in a second, outer sleeve 32 to further protect coil 29. Inner and outer sleeves 31 and 32 are made from a non-conductive material. In one example, inner and outer sleeves 31 and 32 are made from plastic.

The relative motion between shoe 22 and conductor coil 29 is monitored by means of magnetic field coupling with the use of conventional eddy current instrumentation. The use of a target and a suitable excitation frequency for the coil minimize the induction of eddy currents into the surrounding tube.

The length of conductor coil 29 is selected to minimize coil interaction with the magnetite layer and the tubing in which the probe apparatus is inserted for use. Additionally, surface-following module 20 can include shielding material to further minimize interaction of coil 29 with the magnetite layer and the tubing. In accordance with one embodiment of the invention, shielding can be provided in the form of a cylindrical sleeve 34 located around the outside diameter of conductor coil 29, and outer sleeve 32 (if present), as shown in FIG. 2(b). Cylindrical sleeve 34 is approximately the same length as coil 29 and can be made of copper or any other electrically conductive material.

Surface-following module 20 incorporates means for maintaining the surface-following properties of the probe such that changes in tube diameter cause corresponding changes in the separation of the coil and target. Specifically, surface-following module 20 is constructed to ensure that an outer surface of biased shoe 22 remains in contact with an internal surface of the tube. In accordance with one embodiment of the invention, as depicted in FIGS. 2a and 2b, the means for maintaining the surface-following properties of the module comprises a second, fixed shoe 40 located on the opposite side of the body from biased shoe 22. This configuration allows the probe to be sensitive to tube diameter variations, and/or inside diameter deposit thickness variations.

In accordance with an alternative embodiment of the invention, the means for maintaining the surface-following properties comprises one or more pairs of floating shoes. In this embodiment, the conductor coil is mounted in one of the floating shoes and the target is mounted in the body of the surface-following module, or in one of the other floating shoes.

In accordance with one embodiment of the invention, the spring-mounted shoe and/or the fixed shoe of the first module are replaceable. The replaceability of the shoes allows users to customize the probe to adjust for variations in tube inside diameter or deposit thickness. This is required in those cases where the thickness is beyond the range of the shoe travel. In addition, it is possible to change shoes as they wear out. Furthermore, the shoe dimensions can be varied to any size and shape to account for the type of surface variations to be measured. Smaller shoe length permits a finer resolution of localized variations, whereas longer lengths would only be sensitive to larger variations in diameter.

An additional advantage of including at least one removable shoe, is that removal of the shoe can allow easy access to the interior of the surface-following module to permit maintenance of the device and/or allow the target to be changed as necessary.

In accordance with the embodiment of the invention depicted in FIG. 2b both biased shoe 22 and fixed shoe 40 are removable and are held in place by shoe covers 44 and 46. The shoe covers 44 and 46 thread onto body 30 at opposite ends of surface-following module 20 and each extend over a portion of biased shoe 22 and fixed shoe 40 such that they are held in place.

Optionally, protective inserts are included in the shoes and guides to minimize wear of the surfaces and to maintain probe centering in harsh and/or abrasive environments. In a particular example, as depicted in FIG. 2b, the protective inserts are ceramic inserts 48.

First module 20 senses diameter changes along one circumferential orientation. This assumes that ID magnetite deposit thickness is consistent about the circumference of the tube. Metallography studies of pulled tubes have shown this assumption to be valid. If required, however, additional pairs of shoes (i.e., one fixed and one biased, or spring-mounted) can be incorporated in first module 20 to sense the diameter changes along other circumferential orientations.

First module 20 is connected to a computer system for collecting and transforming voltage output resulting from the interaction between coil 29 and target 26. Wires and cables used for computer connections extend through channel 50 within body 30 and continue along the length of the push tube (not shown). The wires and cables are covered by shoe cover 46 upon assembly of the device.

One example of a computer system that is currently commercially available and suitable for use with the apparatus of the present invention is the Zetec MIZ-80id eddy current instrument.

Eddy Current Module

Second module 60 consists of a conventional eddy current probe, such as a bobbin probe, also connected to the eddy current instrument but on a separate channel.

Figure 3:
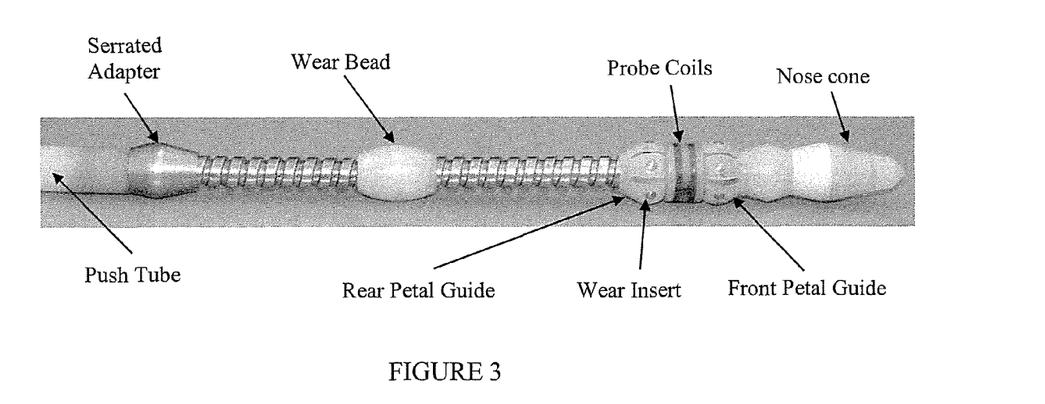
FIG. 3 is a photograph of a standard eddy current bobbin probe suitable for use in the probe apparatus of the present invention.

A typical design example of the bobbin probe is given in FIG. 3, which is the current industry standard for inspection of steam generator and heat exchanger tubing. The bobbin probe depicted in FIG. 3 can be adapted for attachment to a first, surface following module by replacement or adaptation of the nose cone and front petal guide to facilitate attachment to the body of the first, surface following module. An example of such a combination is shown in FIGS. 1 and 2a. As depicted in FIGS. 1 and 2a, second module 60 can consist of a standard bobbin probe having rear guide 62, followed by a flexible section 64 comprising wear beads 66. The probe apparatus further includes an end portion 80 for receiving a push tube (not shown), permanently or removably, to push the probe into the tube being tested The probe in second module 60, which provides the conventional data required in a typical inspection technique, can be used to monitor the variations in ID magnetite thickness and permeability, and provides a means for locating the axial position of the probe within the tube. In this regard, the eddy current probe may be of any design or type, not limited to a simple bobbin probe. In a specific example, second module 60 is a bobbin probe that includes a titanium casing (not shown) to protect the bobbin-probe coils.

Other probe types such as magnetic bias probes, array probes or rotating probes, or other probe technologies such as ultrasound, transient or remote field eddy current can be used in conjunction with one or more surface-following modules. The selection of probe type or technology is dependent on the application and what information is to be correlated to diameter. Each different application can require unique design or can be interchangeable, such that different probe types and technologies can be used with the same surface-following module or modules.

Second module 60 is connected to the same computer system as first module 20. The variations in the ferromagnetic deposit, such as ID magnetite, can then be correlated with the accurate diameter measurements provided by first module 20.

In accordance with one embodiment of the invention, the probe apparatus is designed for use in non-ferromagnetic metallic tubing, such as but not limited to Inconel™ 600 or Incoloy™ 800. In accordance with an alternative embodiment, the probe apparatus is designed for usage in mildly ferromagnetic metallic tubing, such as, but not limited to Monel™ 400, and non-conductive tubing.

Further, in accordance with a particular embodiment of the invention, the probe described herein is intended for tubes with nominal inside diameter greater than 0.350". However, the probe assembly is adaptable such that it can be conveniently used in tubes of various diameters.

Application

In use, the first module effectively calibrates the probe in the second module. This relationship is used to infer the actual thickness of the ID magnetite deposits. If the deposit under test is non-ferromagnetic and non-conductive, then the surface-following module can be used independently to measure the deposit thickness or quantify the reduction of the inside diameter of the tube.

No external reference probes are required to operate the surface following module. The eddy-current module and surface-following module are operated at the same frequencies; however, different timeslots are used to avoid crosstalk. FIG. 4 provides an example of an examination technique specification sheet (ETSS). This ETSS describes the data acquisition process. It should be noted that in this example, the eddy-current probe was a bobbin probe and the amplifier gain for the absolute channels of the bobbin probe was lowered from the standard bobbin technique to avoid signal saturation when sensing thick sections of magnetite. As noted above, other eddy current instruments can be used in the probe apparatus of the present invention, however an adapter and an external reference would be required.

In accordance with one embodiment of the invention, the probe can be used to scan a small number of tubes to measure the profile of the magnetite within an area of the steam generator. This information would be used to report directly the magnetite thickness of those tubes inspected and/or to determine conversion factors that could be applied to the remaining bobbin-probe data. If combined with the Oxiprobe information, the data could also be used to verify the density value required by the other techniques.

In accordance with another aspect of the present invention, there is provided a method of performing internal diameter measurements using a probe apparatus as described herein and a dent calibration standard. A specific example of such a method comprises the following steps:

1. Setup and prepare the eddy current instrumentation at the location of the inspection;
2. Connect the probe and verify it is operating correctly;
3. Insert the probe into the dent calibration standard;
4. While ensuring that both modules are away from any calibration references, null the probe to balance the electronic bridge;
5. Review the calibration reference data from the calibration standard and adjust the dent signals so that they deflect vertically as the probe passes over a dent;
6. Push the probe entirely through the dent calibration standard;
7. While pulling at a constant speed, record the data as the probe is pulled through and out of the dent calibration standard;
8. Review the data, and repeat this scan to ensure that good data is recorded;
9. Measure the voltage changes for each dent, and plot the diameter reduction versus the voltage, to produce a curve similar to that in FIG. 12. The origin represents the diameter of the dent sample as the reference point;
10. Insert the probe through the dent calibration standard and into the tube to be measured;
11. While pulling at a constant speed, record the data as the probe is pulled through the tube to be measured and through the dent calibration standard;
12. Repeat on all tubes to be measured;
13. To analyse the measured data, measure the voltage from the dent standard's nominal ID position to the nominal ID of the tube being measured. This provides a value for the tube's diameter increase or decrease with respect to the dent standard;
14. Plot this operating point on the calibration curve (FIG. 12), and can be above or below the origin;
15. Measure and plot the voltages due to ID magnetite relative to the operating point on the calibration curve. In this way, the measurement is adjusted by the differences between the inside diameters of the tubes;
16. The thickness estimate can be now read off the calibration curve.

The probe apparatus and method of the present invention are particularly useful in identifying and measuring magnetite deposit on the ID of heat exchange or steam generator tubes. However, the probe apparatus of the present invention can also be used in electrical utilities for the purpose of inspecting their steam generators during scheduled maintenance outages.

Generally, the probe apparatus can be used for measuring conductive and non-conductive deposits in any cylindrical equipment. The eddy current module of the probe apparatus of the present invention can also be used to measure tube characteristics or flaws such as, but not limited to, cracks, dents, bulges and expansions, depending on the selected eddy current probe type.

To gain a better understanding of the invention described herein, the following examples are set forth. It should be understood that these examples are for illustrative purposes only. Therefore, they should not limit the scope of this invention in any way.

EXAMPLES

Figure 5:
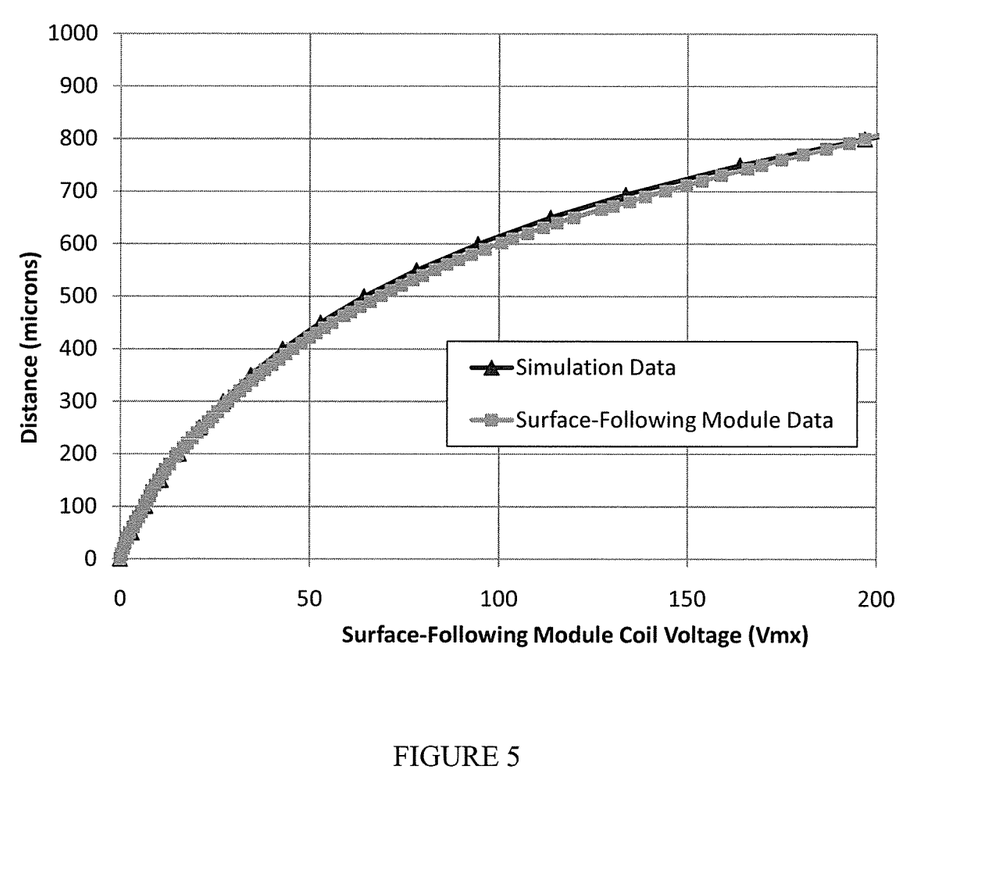
FIG. 5 graphically depicts a comparison of a surface-following module displacement and electromagnetic modelling results.

To begin an initial probe design, MagNet v6 3D finite-element electromagnetic modelling software from Infolytica Corporation was used to model the interactions between the surface-following module coil and the target. Coil geometry, target geometry and properties, and spacing considerations were modelled and a solution was developed. The length of the coil was adjusted to lower the coil interaction with the magnetite layer and the tubing in which the probe was inserted. FIG. 5 shows the electromagnetic modelling result of coil voltage output versus target proximity. FIG. 5 also compares the modelling to the experimental results described below. Based upon the modelled coil, physical coils were produced and their resistance and inductance were measured.

Figure 6:
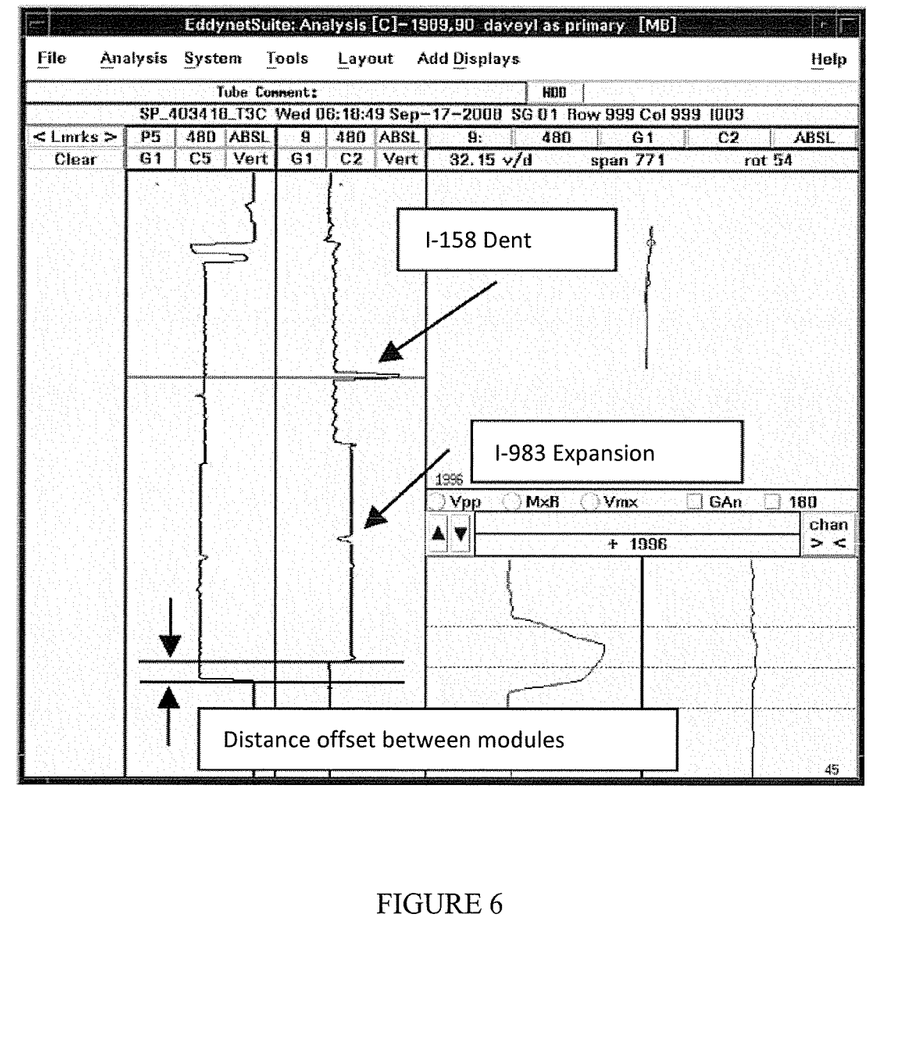
FIG. 6 depicts surface-following module and bobbin module probe output without slewing (Tubes I-158 and I-983).
Figure 7:
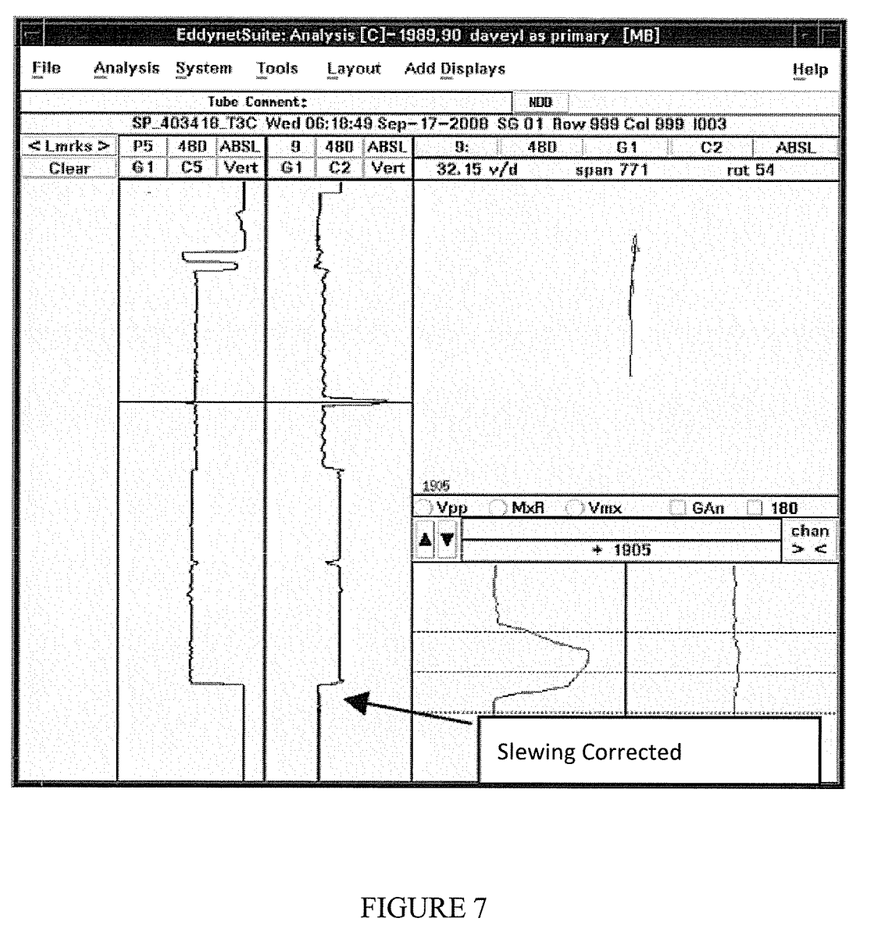
FIG. 7 depicts surface-following module and bobbin module probe output after data slewing (Tubes I-158 and I-983).

An initial probe consisting only of the surface-following module and was used to verify the modelling results and provide proof of the concept. Initial testing with the prototype surface-following module was successful and FIG. 5 shows the comparison between the bench-top surface-following module and the computer modelling results. The data from the bench-top probe was collected by squeezing the shoes with a micrometer, recording the displacement and measuring the signal amplitude generated from the probe. Based on these results, a complete assembly with both modules and a 15.24 m (50') long push-tube was built. This complete probe prototype was tested on a dented sample (labelled I-2205) and tubes that had laboratory-coated layers of ID magnetite (labelled I-806, I-810, and I-815). The dented sample was constructed to provide a series of diameter reductions over the range of motion for the surface-following module. This sample, I-2205, is considered a calibration sample for ID measurement purposes. Table 1 summarizes the dents, their signal responses and associated physical measurements. FIG. 6 shows the output from the probe. The left strip chart shows the bobbin-module response to the dent in I-158 (C3-8 probe standard) and the right strip chart shows the surface-following-module response. The dent in I-158 had a diameter reduction of 500 μm. In these plots the signals from the diameter reduction have been rotated vertically to allow for measurements to be made with the maximum vertical voltage. Since the two modules are separated axially along the probe body, data slewing can be used to align the data from the same sections of tubing. FIG. 7 shows the results from the probe after applying data slewing.

TABLE 1

Summary of Dent Standard I-2205 Measurement Information

| Indentation Location | Diameter Reduction (μm) | Surface-Following Module Indentation Voltage (v) |
|---|---|---|
| A | 359 | 100.00 |
| B | 326 | 82.95 |
| C | 263 | 58.80 |
| D | 245 | 47.66 |
| E | 165 | 24.46 |
| F | 103 | 14.13 |

Figure 8:
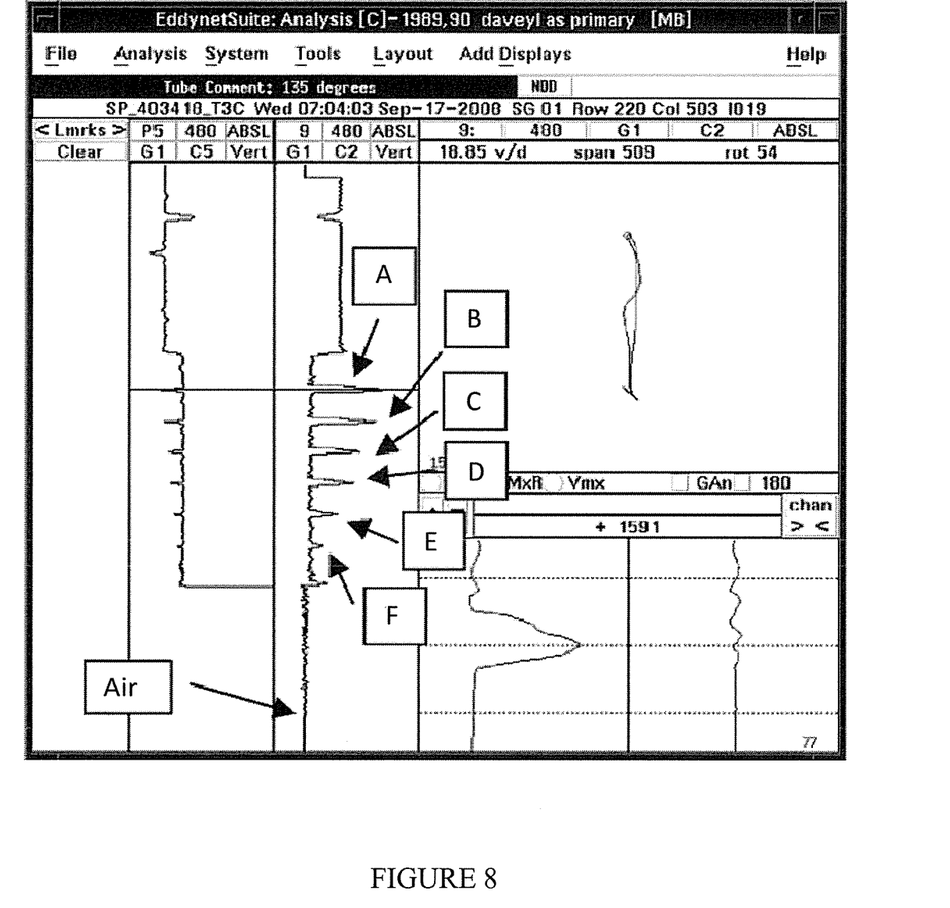
FIG. 8 depicts data from dent standard I-2205.
Figure 9:
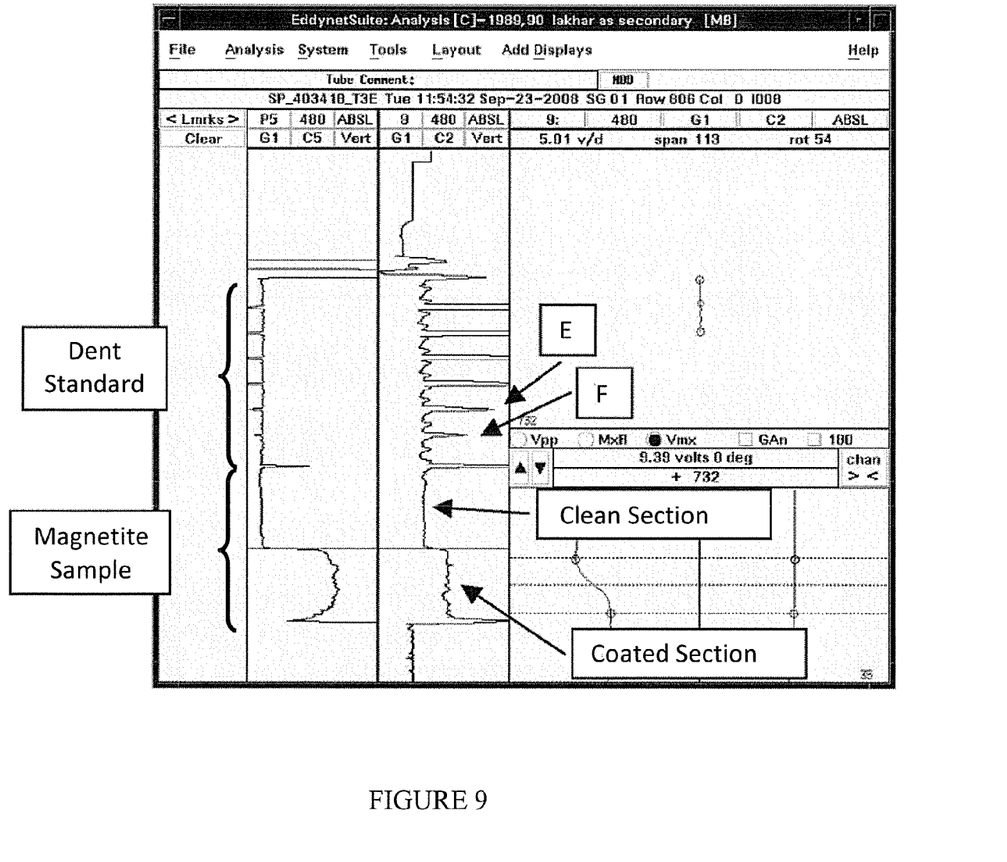
FIG. 9 depicts data from laboratory produced magnetite sample I-806 (56 μm).
Figure 10:
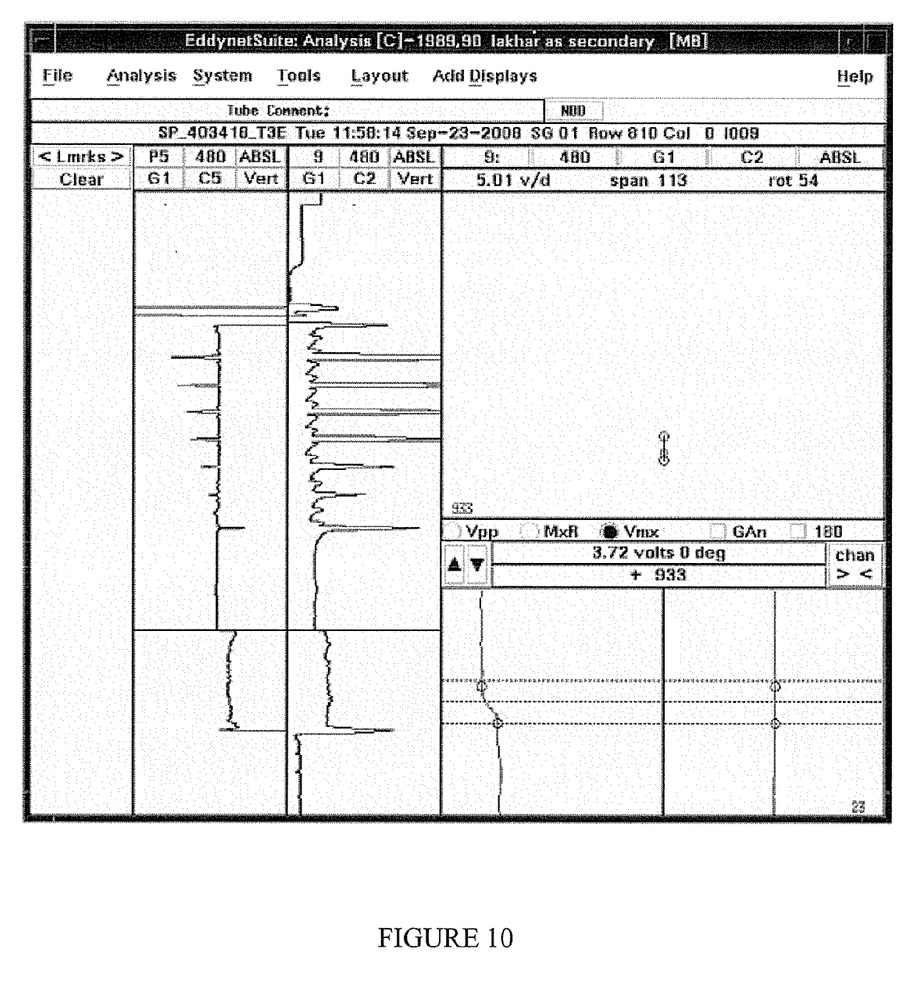
FIG. 10 depicts data from laboratory produced magnetite sample I-810 (24 μm).
Figure 11:
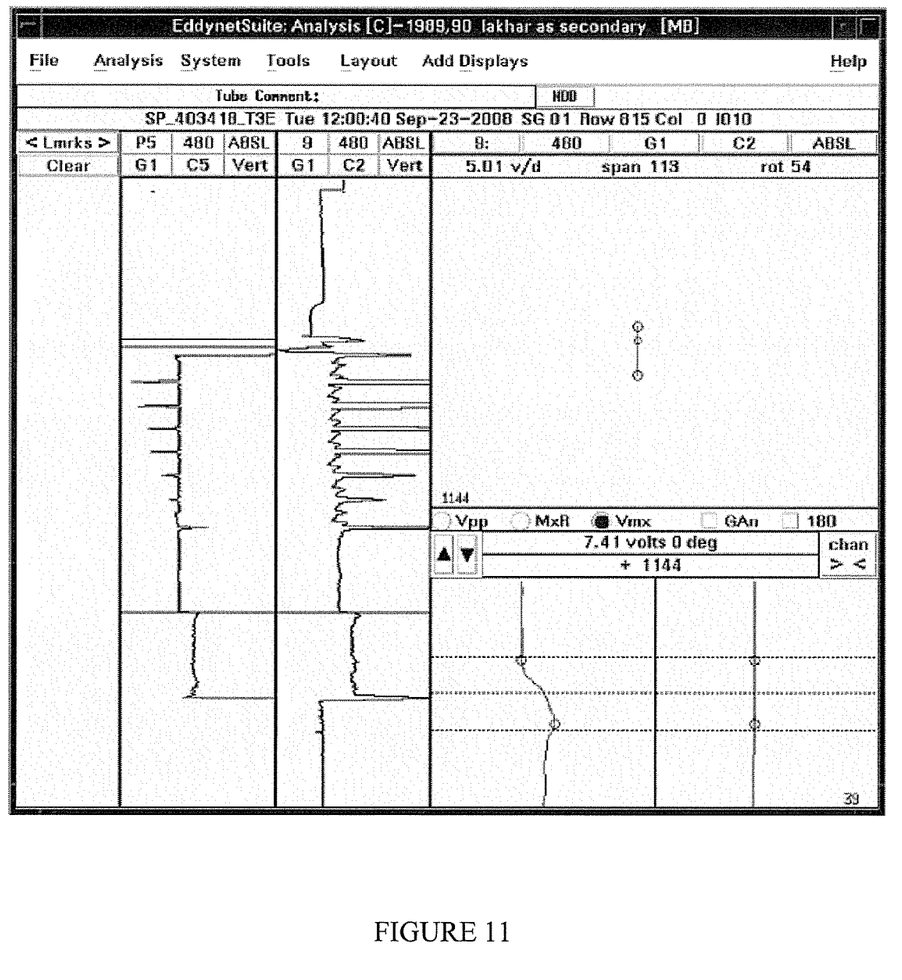
FIG. 11 depicts data from laboratory produced magnetite sample I-815 (45 μm).

FIG. 8 shows the results from the six diameter reductions in I-2205 described in Table 1. The laboratory magnetite inspection results are shown in FIGS. 9, 10, and 11. FIG. 9 shows the data from sample I-806; this tube's ID was coated twice with magnetite. FIG. 10 and FIG. 11 show samples I-810 and I-815 respectively, in this case both tube IDs were coated once with magnetite.

Analysis

Figure 12:
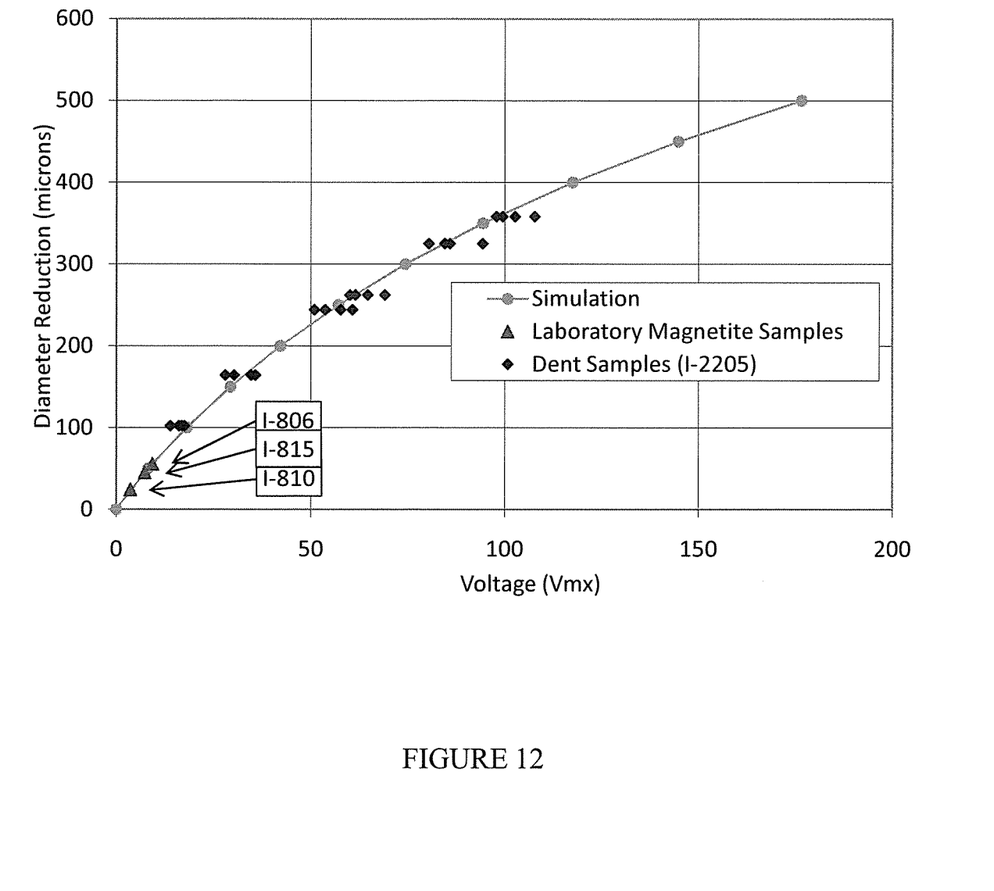
FIG. 12 depicts a calibration curve prepared using dent standard I-2205 and including location of magnetite samples I-806, I-810 and I-815.

To analyse the prototype-probe data, a known diameter was required for calibration. This diameter information was obtained from the known nominal diameter of the dent sample I-2205. FIG. 12 shows the laboratory results from the dented sample compared to the results from the simulation. The results show very good agreement. FIG. 12 also shows the thickness estimates for tube I-806 (56 μm), I-810 (24 μm), and I-815 (45 μm). These results are based upon a calibration process that utilizes the diameter of the dent sample as a reference point, represented on FIG. 12 as the origin. In scans of unknown tubes, if the tube has a different inside diameter than the dent sample, then the measurements would need to be made in the following steps. First, the voltage is measured from the dent sample's nominal ID position to the nominal ID of the tube under test. This provides a value for the tube's diameter increase or decrease with respect to the dent sample I-2205, and is plotted on the calibration curve (FIG. 12). Second, the voltages due to ID magnetite are measured relative to this point on the calibration curve for that tube. In this way, the measurement is adjusted by the differences between the inside diameters of the tubes. For field deployments, a dent calibration tube similar to I-2205 would be supplied with the probe.

FIGS. 9, 10 and 11 show the responses from the dent sample with the three-magnetite samples. In this case, the ID measurements are relative to zero in FIG. 12, since their diameters are very similar to the dent sample.

During the initial stages of developing an analysis method, attempts were made to relate the amount of shoe displacement to the condition where the shoes are fully extended outside of the sample since this was a simple reference to obtain. When the data was analysed in this fashion the laboratory results disagreed with the modelling results. This discrepancy was due to electromagnetic coupling of both the surface-following module coil and its reference coil to the tubing. Further modelling has developed a method of shielding the surface-following module coil. Shielding can be provided by adding a cylindrical sleeve made of copper or any other electrically conductive material around the outside diameter of the conductor coil, of the same length as the coil, as shown in the diagram of FIG. 2(b).

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A probe apparatus comprising a surface-following probe, said surface-following probe comprising:
   (a) a probe body,
   (b) one or more shoe pairs, wherein each shoe pair consists of a biased shoe attached to said probe body and a fixed shoe attached to said probe body,
   (c) a target mounted on the biased shoe of each of said one or more shoe pairs, wherein said target comprises a material that is conductive and ferromagnetic, conductive and non-ferromagnetic, or non-conductive and ferromagnetic, and
   (d) a conductor coil fixed to said body to allow relative movement of said biased shoe electromagnetically coupled with each target to produce a voltage output indicative of motion of the biased shoe relative to probe body
   (e) an eddy-current probe coupled to said probe body.

2. The probe apparatus according to claim 1, wherein said eddy-current probe is a bobbin probe.

3. The probe apparatus according to claim 1, wherein said biased shoe is a spring-mounted shoe.

4. The probe apparatus according to claim 1, wherein said biased shoe and said fixed shoe each include one or more protective insert.

5. The probe apparatus according to claim 3, wherein said protective insert is ceramic.

6. The probe apparatus according to claim 1, which comprises more than one shoe pair.

7. The probe apparatus according to claim 1, which additionally comprises a push tube.

8. The probe apparatus according to claim 1, wherein said target is puck-shaped, cylindrical or comprises a puck-shaped portion and a cylindrical portion.

9. The probe apparatus according to claim 8, wherein said target comprises a puck-shaped portion and a cylindrical portion and wherein said cylindrical portion extends within a portion of said conductor coil.

10. The probe apparatus according to claim 1, wherein said target is made from a material that is conductive and ferromagnetic, conductive and non-ferromagnetic, non-conductive and ferromagnetic, or a combination thereof.

11. The probe apparatus according to claim 10, wherein said target is made from ferrite or steel.

12. A method of determining the thickness of an inside diameter, conductive deposit within a tube, said method comprising the steps of:
    (a) determining the internal diameter of the tube at a location within the tube by measuring outward movement of a shoe with a conductor configured to allow relative movement of the shoe;
    (b) performing eddy current testing at the location; and
    (c) correlating the internal diameter determined in step (a) with the output from step (b) to calculate the thickness of the inside diameter, conductive deposit within the tube.

13. A kit for use in determining the thickness of an inside diameter, non-conductive deposit within a tube, said kit comprising (i) a probe apparatus according to claim 1; and (ii) one or more dent calibration tube.

14. A kit for use in determining the thickness of an inside diameter, conductive deposit within a tube, said kit comprising (i) a probe apparatus according to claim 1; and (ii) one or more dent calibration tube.

* * * * *